United States Patent [19]

Hebeler, Jr.

[11] Patent Number: 5,054,484
[45] Date of Patent: Oct. 8, 1991

[54] TRACHEOSTOMY DEVICE

[76] Inventor: Robert F. Hebeler, Jr., 3720 Beverly Dr., Dallas, Tex. 75205

[21] Appl. No.: 616,855

[22] Filed: Nov. 21, 1990

[51] Int. Cl.$^5$ ............................................. A61M 16/00
[52] U.S. Cl. ........................... 128/207.16; 128/207.14; 128/207.15
[58] Field of Search ....................... 128/200.26, 207.14, 128/207.15, 207.16, 207.29; 623/9

[56] References Cited

U.S. PATENT DOCUMENTS

| | | | |
|---|---|---|---|
| 1,633,705 | 6/1927 | McKesson | 623/9 |
| 3,721,233 | 3/1973 | Montgomery et al. | 128/351 |
| 3,993,059 | 11/1976 | Sjostrand | 128/207.16 |
| 4,274,162 | 6/1981 | Joy et al. | 623/9 |
| 4,280,492 | 7/1981 | Latham | 128/207.15 |
| 4,315,505 | 2/1982 | Crandall et al. | 128/200.26 |
| 4,340,046 | 7/1982 | Cox | 128/207.17 |
| 4,494,252 | 1/1985 | Chaoui | 623/9 |
| 4,627,433 | 12/1986 | Lieberman | 128/207.16 |
| 4,794,924 | 1/1989 | Eliachar | 128/207.16 |
| 4,795,465 | 1/1989 | Marten | 623/9 |
| 4,850,349 | 7/1989 | Farahany | 128/207.15 |
| 4,877,025 | 10/1989 | Hanson | 128/207.16 |

Primary Examiner—Aaron J. Lewis
Attorney, Agent, or Firm—Johnson & Gibbs

[57] ABSTRACT

A tracheal T-tube stent is formed from a flexible, resiliently yieldable material and has a hollow, open-ended tubular body portion which is coaxially insertable into the trachea through a suitable neck incision, and a transverse tubular portion which projects outwardly through the incision and has a small side wall opening therein. The distal end portion of a small inflation lumen having an air inlet check valve fitting at its proximal end is extended inwardly through the side wall opening, runs inwardly along the interior side surface of the transverse tube portion and upwardly along the interior side surface of the top end of the body portion, and is connected at its distal end to an inflation balloon disposed within the top end of the T-tube body. With the T-tube in place within the trachea, and the balloon deflated, the T-tube functions as an ordinary tracheal stent to hold the trachea open and permit normal patient breathing. By simply inflating the balloon the upper tube body end is internally occluded, thereby permitting the T-tube to be utilized as a ventilator fitting when desired. In this manner, the conventional use of a curved tracheostomy tube, with its attendant tracheal scarring, may be advantageously eliminated.

10 Claims, 1 Drawing Sheet

TRACHEOSTOMY DEVICE

BACKGROUND OF THE INVENTION

The present invention relates generally to medical devices, and more particularly relates to tracheal stent devices.

There are many indications for tracheostomy, in which a device known as a tracheostomy tube is typically inserted into the trachea for inhalation purposes. The tracheostomy tube is basically a curved plastic tube fitted adjacent its distal end (which is inserted downwardly into the trachea through a suitable next incision) therein with an external balloon or cuff element which may be selectively inflated within the trachea to retain the tube in place and allow for mechanical ventilation. With the tracheostomy tube in place, the outer tube end is operatively connected to a ventilator which functions to cyclically force air downwardly through the inserted tube into the tracheal passage portion below it, and into the patient's lungs.

Conventional balloon-tipped tracheostomy tubes often cause interior tracheal scarring which restricts the tracheal passage. This scarring typically arises due to the fact that the curved tracheostomy tube does not conform to the essentially straight tracheal anatomy, and leads to pressure necrosis of the wall of the trachea, and from the pressure forces imposed on the interior surface of the trachea by the inflated retention balloon.

Upon removal of the tracheostomy tube, this interior scarring, which tends to restrict the trachea, may necessitate the subsequent insertion into the trachea of a device known as a T-tube stent, or a "Montgomery tube", which functions to hold the scarred and restricted tracheal portion open and prevent it from unduly restricting patient breathing. The typical T-tube stent utilized in this manner is illustrated in U.S. Pat. No. 3,721,233 to Montgomery et al. and includes a hollow, open-ended tubular body portion which is coaxially inserted into the trachea, and a hollow transverse central leg portion which passes outwardly through the tracheal insertion incision and is suitably stoppered at its outer end.

While the subsequent use of conventional T-tube stents in this manner is quite beneficial in holding open scar tissue-restricted tracheal passage areas during patient recuperation, it does not permit the use of a ventilator to assist the patient's breathing. Air forced into the outwardly projecting transverse stent portion cannot be effectively forced downwardly into the patient's lungs because both the upper and lower ends of the inserted T-tube body within the trachea are open, and air passes preferentially out the mouth because of less resistance.

From the foregoing it can be readily seen that the conventional sequential use of curved tracheostomy tubes and T-tube stents in the tracheal area is, for a variety of reasons, not wholly satisfactory. It is accordingly an object of the present invention to provide improved apparatus less traumatic to the trachea which can also hold the trachea open and permit the use of an inhalator to assist a patient's breathing when necessary. This then may prevent scarring produced by conventional hard plastic tracheostomy appliances as well as allow a greater application to patients with early scarring who still require ventilatory assistance.

SUMMARY OF THE INVENTION

In carrying out principles of the present invention, in accordance with a preferred embodiment thereof, an improved flexible T-tube stent is provided which has a hollow, open-ended tubular body portion with top and bottom longitudinal sections. Projecting transversely outwardly from the body, between its top and bottom longitudinal sections, is a hollow tubular arm portion of the stent which has a small side wall opening therein and an open outer end that may be suitably plugged or connected to the outlet of an inhalator.

An inflation balloon is disposed within the upper stint body section and is operatively connected to the distal end of a small inflation lumen. From its distal end connection to the balloon, the inflation lumen extends along and is suitably secured to the interior side surfaces of the upper body end section and the transverse arm portion, and then passes outwardly through the arm portion side wall opening, the proximal end of the lumen being provided with an air inlet check valve fitting securable to an air syringe operable to inflate the balloon.

To use the T-tube stent of the present invention, the stent body is bent and inserted through a suitable neck incision into the trachea so that the inserted body is coaxially disposed within the trachea, with the top body section facing upwardly therein and the transverse stent arm section projecting outwardly through the incision.

When the balloon is inflated it internally occludes the top end section of the inserted stent body, thereby permitting the inserted stent to function as a ventilator fitting—i.e., to perform the function of a conventional curved tracheostomy tube—when ventilator air is cyclically flowed inwardly through the open outer end of the outwardly projecting stent arm portion. The incoming ventilator air is prevented by the inflated balloon from flowing upwardly through the stent body, being forced instead to flow downwardly through the trachea into the patient's lungs.

Importantly, since the inserted stent body does not utilize an external inflatable balloon or cuff to retain it in place within the trachea, the pressure-induced tracheal scarring normally associated with a curved tracheostomy tube used with a ventilator is essentially eliminated.

When ventilator assistance is discontinued, the internal stent body balloon is simply deflated, and a suitable plug member is inserted into the outer end of the transverse stent arm. The stent may then be used in its usual manner—i.e., to hold open the portion of the trachea into which the stent body is inserted to thereby permit normal patient breathing. To rapidly convert the inserted stent back to its ventilator fitting mode, all that is necessary is to re-inflate its internal occluding balloon, remove the plug from the transverse stent arm, and connect the arm to an inhalator.

Weaning from ventilatory assistance should be facilitated as the patient will be breathing through a larger diameter tube than conventional appliances can permit.

Another benefit is that periodic deflation of the balloon can be performed with a patient on the ventilator to allow removal of caustic oral secretions which typically collect above the balloon cuff on standard tracheostomy devices.

It can readily be seen that the improved T-tube stent of the present invention provides a variety of advantages compared to the sequential use of a curved tracheostomy tube, with its external retention cuff, and an

DETAILED DESCRIPTION

Figure 1:
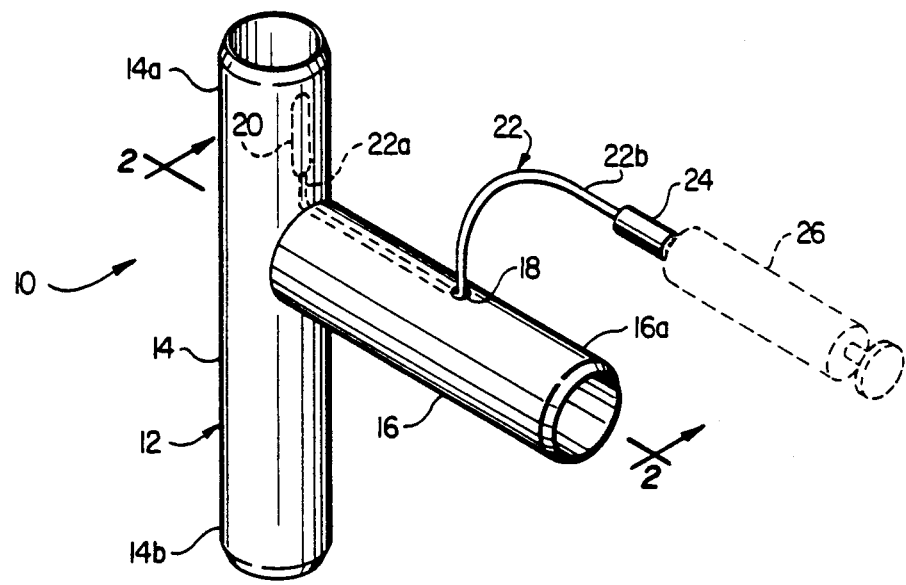
FIG. 1 is a perspective view of an improved tracheal T-tube stent device which embodies principles of the present invention.

Perspectively illustrated in FIG. is an improved tracheostomy device 10 which embodies principles of the present invention. Device 10 includes a T-tube stent 12 formed from a soft, resiliently yieldable material, such as silicone rubber, and having a hollow, open-ended tubular body portion 14 with opposite top and bottom longitudinal sections 14$^a$ and 14$^b$. A hollow tubular arm portion 16, having an open outer end 16$^a$, extends transversely outwardly from a longitudinally intermediate portion of the stent body 14 and has a small circular side wall opening 18 formed in its upper side intermediate its inner and outer ends. The interior of the transverse arm 16 communicates with the interior of the stent body 14.

Figure 2:
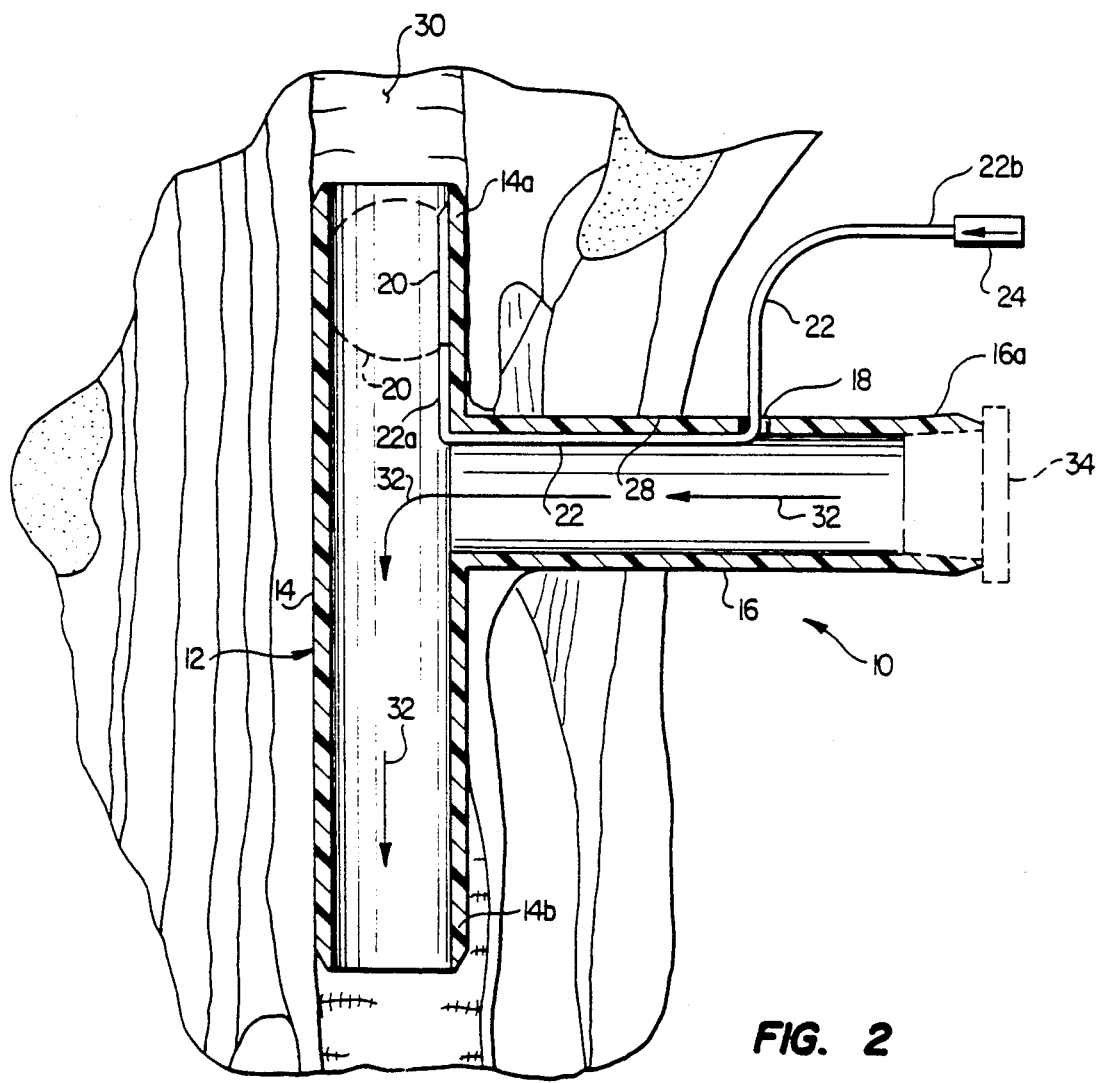
FIG. 2 is an enlarged scale cross-sectional view through the stent, taken along line 2—2 of FIG. 1, in place within the trachea.

For purposes later described, a small inflation balloon 20 is disposed within the top longitudinal section 14$_a$ of the stent body 14 and is operatively secured to the distal end 22$_a$ of a small inflation lumen 22. As illustrated in FIG. 2, from its connection to the balloon 20, the lumen 22 extends along and is suitably secured to the interior side surfaces of the top stent body section 14$_a$ and the transverse arm 16, a proximal end portion 22$_b$ of the lumen 22 being passed outwardly through the side wall opening 18, with the outer end of the lumen portion 22$_b$ being operatively secured to a conventional air inlet check valve fitting 24 which may be connected to a source of pressurized air such as an air syringe 26 (FIG. 1). By forcing air from the syringe 26 through the inflation lumen 22, the balloon 20 may be inflated, (as shown in dotted lines in FIG. 2) to internally occlude the top section 14$_a$ of the stent body 14 to preclude air movement inwardly or outwardly through such top section. Alternatively, the check valve 26 may be operated in a conventional fashion to permit pressurized air to escape outwardly through the proximal lumen end 22$_b$ to deflate the balloon 20 to its solid line position in FIG. 2. This clears the top section 14$_a$ of the stent body and permits air flow in either vertical direction therethrough.

To use the device 10 the stent body 14 is suitably bent and, in a conventional manner, inserted through a neck incision 28 (FIG. 2) into a patient's tracheal passage 30 to operatively position the stent body 14 coaxially within the trachea with the top body section 14$_a$ facing upwardly (i.e., toward the head of the patient), and the transverse arm portion 16 projecting outwardly through the incision 28. Inserted in this manner, the T-tube stent 12 may be utilized as a ventilator fitting to mechanically assist the patient in breathing, or to simply hold open the tracheal portion into which it is inserted and permit the patient to breath normally.

With the stent 12 inserted into the trachea 30 as illustrated in FIG. 2, the stent may be used as a ventilator fitting simply by inflating the occluding balloon 20 to its dotted line position and connecting the outer end 16$_a$ of the outwardly projecting transverse arm 16 to a mechanical inhalator. Operation of the ventilator cyclically forces air 32 inwardly through the arm 16 and downwardly through the stent body 14 through a lower portion of the trachea into the patient's lungs. Importantly, since the inflated balloon 20 blocks the interior of the top stent body end section 14$_a$, nearly all of the inflowing air 32 is downwardly directed into the patient's lungs. Any volume lost due to air passing around the tube can be compensated for by ventilator adjustments.

When the need for mechanical breathing assistance ceases, the balloon 20 is deflated to its solid line position in FIG. 2, the transverse stent arm 16 is disconnected from the ventilator, and a suitable plug member 34 is later inserted into the outer end 16$_a$ of the stent arm 16. Since the deflated balloon 20 again opens the top longitudinal section 14$_a$ of the stent body 14, the patient may breath normally upwardly and downwardly through the stent body 14 while it continues to hold open the tracheal portion into which it has been inserted. Should the need arise to again provide the patient with mechanical breathing assistance, the device 10 may be rapidly converted to an inhalator fitting simply by removing the plug 34, connecting the outer end 16$_a$ of the transverse arm 16 to the ventilator, and re-inflating the occluding balloon 20 to its dotted line position to again block the top section 14$_a$ of the stent body 14.

It can be readily seen that the single device 10 of the present invention functions both as a conventional tracheal T-tube stent which permits essentially normal patient breathing, and as a ventilator fitting which facilitates the mechanical assistance of such breathing. Compared to the normal method of sequentially utilizing a curved tracheostomy tube, removing the tube, and then replacing it with a conventional T-tube stent, the present invention provides a variety of advantages.

For example, tracheal scarring (caused by the rigid curved tracheostomy tube with its inflatable external cuff) is minimized if not eliminated, only one device need be inserted into the tracheal passage 30, and the conversion between normal patient breathing and ventilator-assisted patient breathing is more quickly achieved. The illustrated device 10 of the present invention is easy and relatively inexpensive to fabricate, is easy to use, and provides for very reliable and safe operation.

The foregoing detailed description is to be clearly understood as being given by way of illustration and example only, the spirit and scope of the present invention being limited solely by the appended claims.

What is claimed is:

1. A combination ventilator fitting/tracheal stent device comprising:

a hollow, generally T-shaped tracheal stent formed from a flexible, resiliently yieldable material and having:

a tubular, open-ended body portion having top and bottom longitudinal sections, said body portion being insertable, through a neck incision, into the tracheal passage of a patient to coaxially position said body portion therein with said top longitudinal section extending toward the head of the patient, and a tubular arm portion extending transversely outwardly from a longitudinally intermediate section of said body portion and having an open outer end, and an interior which communicates with the interior of said body portion, said arm portion being positioned and configured to project outwardly through the neck incision when said body portion is operably inserted into the tracheal passage; and means for selectively and internally blocking or unblocking said top longitudinal section of said body portion when it is operatively inserted in the tracheal passage, where said stent may be used:

(1) as a ventilator fitting by internally blocking said top longitudinal section of said body portion and connecting said outer end of said arm portion to the outlet of a mechanical ventilator to cyclically flow ventilator air downwardly through said body portion and the tracheal passage into the patient's lungs, or (2) to hold open the tracheal passage section into which said body portion is inserted, and permit essentially normal patient breathing through such tracheal passage section, by unblocking said top longitudinal section of said body portion and plugging said outer end of said arm portion.

2. The combination ventilator fitting/tracheal stent device of claim 1 wherein:

said means for selectively and internally blocking or unblocking said top longitudinal section of said body portion include balloon means disposed within said top longitudinal section, said balloon means being inflatable to internally occlude said top longitudinal section, and deflatable to permit upward and downward air flow through said top longitudinal section, and means for selectively inflating and deflating said balloon means.

3. The combination ventilator fitting/tracheal stent device of claim 2 wherein:

said means for selectively inflating and deflating said balloon means include inflation lumen means for flowing pressurized air from a source thereof into said balloon means, said inflation lumen means extending interiorly through said arm portion and said top longitudinal section of said body portion.

4. Improved tracheal stent apparatus comprising:

a hollow, generally T-shaped tracheal stent member having a tubular, essentially straight, open-ended body portion with top and bottom longitudinal sections, and a tubular arm portion extending transversely outwardly from a longitudinally intermediate section of said body portion, said arm portion having an interior which communicates with the interior of said body portion, an open outer end, and a side wall opening formed through a longitudinally intermediate section of said arm portion;

a balloon member disposed within said top longitudinal section of said body portion, said balloon member being inflatable to internally occlude said top longitudinal section to preclude upward air flow therethrough, and being deflatable to permit upward and downward air flow through said top longitudinal section; and an elongated hollow inflation lumen member having a distal end portion extending interiorly through said arm portion and said top longitudinal section and operatively connected at a distal end thereof to said balloon member, a longitudinally intermediate portion passing through said side wall opening in said arm portion, and a proximal end portion disposed exteriorly of said stent member, whereby said balloon member may be inflated by flowing pressurized air inwardly through said proximal end portion, and deflated by permitting pressurized air to flow outwardly through said proximal end portion.

5. The improved tracheal stent apparatus of claim 4 wherein:

said distal end portion of said inflation lumen extends along and is secured to interior side surfaces of said arm portion and said top longitudinal section of said body portion.

6. The improved tracheal stent apparatus of claim 4 wherein:

the outer end of said proximal end portion of said inflation lumen member is connected to an air check valve fitting removably securable to the outlet of an air syringe.

7. The improved tracheal stent apparatus of claim 4 wherein:

said stent member is formed from a flexible, resiliently yieldable material.

8. A tracheostomy procedure comprising the step of:

forming a neck incision extending into the tracheal passage of a patient;

providing a hollow, generally T-shaped tracheal stent having an essentially straight tubular body portion with top and bottom longitudinal sections, and a tubular arm portion extending transversely outwardly from a longitudinally intermediate section of said body portion;

inserting said body portion into the tracheal passage, through the neck incision, so that said top longitudinal section extends toward the head of the patient and said arm portion extends outwardly through the throat incision;

mechanically assisting the patient's breathing by internally blocking said top longitudinal section of the inserted body portion and cyclically flowing ventilator air inwardly through said arm portion; and permitting patient breathing, without ventilator assistance, through the tracheal section in which said body portion is inserted by unblocking said top longitudinal section and terminating the cyclic flow of ventilator air inwardly through said arm portion.

9. The tracheostomy procedure of claim 8 wherein:

said top longitudinal section of said body portion has a balloon member disposed therein, said step of internally blocking said top longitudinal section is performed by inflating said balloon member in a manner causing the inflated balloon member to internally occlude said top longitudinal section, and said step of unblocking said top longitudinal section includes the step of deflating said balloon member.

10. The tracheostomy procedure of claim 9 wherein:

said arm portion has a side wall opening therein through which an inflation lumen passes and then extends through the interiors of said arm portion and said top longitudinal section, said inflation lumen having a distal end operatively connected to said balloon member, and a proximal end portion disposed exteriorly of said stent, said step of inflating said balloon member is performed by flowing pressurized air from a source thereof inwardly through said proximal end portion of said inflation lumen, and said step of deflating said balloon member is performed by permitting an outflow of pressurized air from said proximal end portion of said inflation lumen.

* * * * *